US00PP25804P2

(12) United States Plant Patent
Osiecki

(10) Patent No.: US PP25,804 P2
(45) Date of Patent: Aug. 11, 2015

(54) ***ALOCASIA* PLANT NAMED 'ALO1'**

(50) Latin Name: ***Alocasia* hybrid**
Varietal Denomination: ALO1

(71) Applicant: Marian Osiecki, Marianna, FL (US)

(72) Inventor: Marian Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 159 days.

(21) Appl. No.: 13/986,613

(22) Filed: May 16, 2013

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Alocasia* cultivar named 'ALO1' is disclosed, characterized by dark green, glossy, sagittate foliage with silver shadowing, and contrasting light pink petioles with distinctive decorative streaks. Plants are vigorous, very easy to grow under low and high light conditions and well as low and high temperature conditions. The new variety is commercially suitable for six inch pot production from a single tissue culture micro plantlet. The new variety is an *Alocasia*, typically produced as an ornamental plant.

1 Drawing Sheet

Latin name of the genus and species: *Alocasia* hybrid.
Variety denomination: 'ALO1'.

BACKGROUND OF THE INVENTION

The new cultivar is a product of a planned breeding program. The objectives of the planned breeding program were to develop new *Alocasia* varieties of small to medium size, with rapid, vigorous growth, early and strong basal branching as well as columnar growth, suitable for 6-8 inch commercial pot production. The inventor additionally sought new varieties with interestingly ornamental foliage, and colorful, strongly contrasting leaf peduncles. The new variety originated from a cross pollination of an unpatented seed parent referred to as 'Aurora' and the pollen parent, an unpatented, unnamed, proprietary variety of *Alocasia lowii*. The crossing was made during May of 2007.

The new variety was discovered by the inventor, Marian Osiecki, a citizen of the US, in October of 2008 in a group of seedlings resulting from the crossing. The new cultivar was found in a commercial greenhouse in Altha, Fla.

Asexual reproduction of the new cultivar 'ALO1' was first performed at a commercial laboratory in Altha, Fla. by tissue culture on Mar. 3, 2009. Subsequent propagation by tissue culture has shown that the unique features of this cultivar are stable and reproduced true to type.

SUMMARY OF THE INVENTION

The cultivar 'ALO1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALO1'. These characteristics in combination distinguish 'ALO1' as a new and distinct *Alocasia* cultivar:

1. Very vigorous and fast growing.
2. Abundant and very early production of basal shoots.
3. Symmetrical, upright and columnar growth habit.
4. Dark green, glossy foliage.
5. Thick, sagittate leaf blades.
6. Veins with broad silver shadowing.
7. Attractive, light pink petioles with brown or green streaks.
8. Very easy to grow under low and high light levels as well in low and high temperatures.
9. 'ALO1' is suitable for production in 6-8" pots from a single tissue culture plantlet.

PARENT COMPARISON

Plants of the new cultivar 'ALO1' are similar to the unpatented seed parent 'Aurora' in most horticultural characteristics. The new variety however differs in the following characteristics:

1. 'ALO1' is more vigorous, more compact than 'Aurora'.
2. 'ALO1' is a smaller plant, 35-40 cm tall in a 6" pot, whereas 'Aurora' is 50-60 cm tall.
3. 'ALO1' is a more symmetrical and narrower plant, 23 cm in diameter in a 6" pot whereas 'Aurora' is 30 cm in diameter.
4. 'ALO1' is fuller, less spread and less open compared to 'Aurora'.
5. 'ALO1' has a columnar growth form whereas is 'Aurora' has a more outwardly spreading growth.
6. The leaf blades of 'ALO1' are smaller, darker, thicker and glossier than the leaf blades of 'Aurora'.
7. Leaf veins of 'ALO1' have a darker and broader silver shadow than 'Aurora'.
8. The lower side of 'ALO1' leaf blade is light burgundy and glossy whereas the lower side of 'Aurora' leaf blade is green and matte.
9. Leaf petioles of 'ALO1' are thicker, stronger and shorter compared to leaf petioles of 'Aurora'.

10. Leaf petioles of 'ALO1' are light pink-green color with well marked brown green streaks whereas the leaf petioles of 'Aurora' are pink with very insignificant green streaks.

Plants of the new cultivar 'ALO1' are similar to the pollen parent, an unpatented, unnamed, proprietary variety of *Alocasia lowii*, in most horticultural characteristics. The new variety however differs in the following characteristics:

1. 'ALO1' is a smaller and more compact plant, 35-40 cm tall in a 6" pot, whereas *A. lowii* is 60-70 cm tall.
2. 'ALO1' branches earlier and more abundantly than *A. lowii.*
3. Plants of 'ALO1' are more symmetrical and narrower in diameter compared to *A. lowii.*
4. Plants of 'ALO1' are fuller and more upright than the sparser, very open form of *A. lowii.*
5. The leaf blades of 'ALO1' are much smaller than leaf blades of *A. lowii.*
6. The leaf blades of 'ALO1' have less silver color between veins compared to *A. lowii.*
7. Leaf petioles of 'ALO1' are shorter and stronger than leaf petioles of *A. lowii.*
8. 'ALO1' has light pink-green leaf petioles with well marked brown-green streaks whereas *A. lowii* has light green to green leaf petioles with green-brown streaks.
9. 'ALO1' has more and smaller leaves compared to *A. lowii* which has fewer and much bigger leaves.

COMMERCIAL COMPARISON

'ALO1' can be compared to the unpatented commercial variety *Alocasia* 'Polly'. Plants of 'Polly' are similar to plants of 'ALO1' in most horticultural characteristics. However 'ALO1' differs from 'Polly' in the following characteristics:

1. 'ALO1' is a more vigorous, taller and faster growing plant than 'Polly'.
2. 'ALO1' is a fuller plant, branches much earlier and more abundantly compared to 'Polly'.
3. 'ALO1' is less spread and less open, more columnar compared to 'Polly'.
4. Leaf blades of 'ALO1' are wider with lighter green color compared to narrower and darker leaves of 'Polly'.
5. The lower side of 'ALO1' leaf blade is light burgundy whereas the lower side of 'Polly' leaf blade is darker burgundy.
6. The leaf margins of 'ALO1' are green and smooth (entire) whereas the leaf margins of 'Polly' are silver and lobed.
7. 'ALO1' leaf petioles are light pink-green with well marked brown-green streaks whereas 'Polly' leaf petioles are light green to green color with a few very light green streaks.
8. Leaves of 'ALO1' are oriented more horizontal compared to more downwardly nodding leaves of 'Polly'.
9. 'ALO1' is more tolerant to disease and stress conditions than 'Polly'.

'ALO1' can be compared to the unpatented species *Alocasia amazonica*. Plants of *Alocasia amazonica* are similar to plants of 'ALO1' in most horticultural characteristics. However 'ALO1' differs from *Alocasia amazonica* in the following characteristics:

1. 'ALO1' is a more vigorous and faster growing plant than *A. amazonica.*
2. 'ALO1' is a fuller plant, branches much earlier and more abundant compared to *A. amazonica.*
3. Plants of 'ALO1' are shorter, less spreading, less open and more columnar compared to *A. amazonica.*
4. Mature leaf blades of 'ALO1' are shorter and lighter green color compared to the longer and darker leaf blades of *A. amazonica.*
5. The lower side of leaf blade of 'ALO1' is light burgundy whereas the lower side of *A. amazonica* is dark burgundy.
6. The leaf margins of 'ALO1' are green and smooth(entire) whereas the leaf margins of *A. amazonica* are sliver and lobed.
7. Leaf petioles of 'ALO1' are light pink-green with well marked brown and green streaks whereas the leaf petioles of *A. amazonica* are light green to green color without visible streaks.
8. Leaves of 'ALO1' have a more horizontal orientation, compared to the downwardly nodding foliage of *A. amazonica.*
9. 'ALO1' is more tolerant to disease and stress conditions than *A. amazonica.*

'ALO1' can be compared to the commercial variety *Alocasia* 'ALO4' application Ser. No. 13/986,605. Plants of 'ALO4' are similar to plants of 'ALO1' in most horticultural characteristics. However 'ALO1' differs from 'ALO4' in the following characteristics:

1. Plants of 'ALO1' are taller and wider than plants of 'ALO4'. Typically plants of 'ALO1' grow to 65 cm in height and 65 cm in width, whereas similar aged plants of 'ALO4' are 48 cm tall and 42 cm wide.
2. Foliage of 'ALO1' is wider, typically having a range from 14 to 19.5 cm compared to a typical width of 11 to 14 cm for 'ALO4'.
3. The varieties differ in foliage coloration: Mature foliage coloration of 'ALO1' as follows: Mature foliage upper side: Near RHS Green139A, but darker. Mature foliage under side: Near RHS Greyed-Purple N186C. Compared to mature foliage of 'ALO4': Mature foliage upper side: Near RHS Greyed-Green N189A. RHS Greyed-Green 188C flushing around veins. Mature foliage under side: Near RHS Greyed-Purple N186B.
4. Petioles of 'ALO1' are colored primarily Greyed-Red; petioles of 'ALO4' are colored primarily Greyed-Purple.

'ALO1' can be compared to the commercial variety *Alocasia* 'ALO5' application Ser. No. 13/986,604. Plants of 'ALO5' are similar to plants of 'ALO1' in most horticultural characteristics. However 'ALO1' differs from 'ALO5' in the following characteristics:

1. Plants of 'ALO1' are taller wider than plants of 'ALO5'. Typically plants of 'ALO1' grow to 65 cm in height, whereas similar aged plants of 'ALO5' are 45 cm tall.
2. The leaf blade of 'ALO1' is shorter, typically having a range from 28 to 35 cm compared to a typical leaf blade length of 40 to 50 cm for 'ALO5'.
3. The varieties differ in foliage coloration: Mature foliage coloration of 'ALO1' as follows: Mature foliage upper side: Near RHS Green139A, but darker. Mature foliage under side: Near RHS Greyed-Purple N186C. Compared to mature foliage of 'ALO5': Mature foliage upper side: Near RHS Greyed-Green N189A. Slightly flushing RHS Greyed-Green 190C around veins. Mature foliage under side: Near RHS Green 143A, heavily flushed over nearly entire surface RHS Greyed-Purple N186C. Margin RHS Green 143A.

BRIEF DESCRIPTION OF THE PHOTOGRAPH

The accompanying photograph in FIG. 1 illustrates in full color a typical plant of 'ALO1' grown in a greenhouse in Altha, Fla. This plant is approximately 9 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'ALO1' plants grown in a climate controlled greenhouse in Altha, Fla., USA. Temperatures ranged from 20° C. to 25° C. at night to 25° C. to 32° C. during the day. No artificial light, photoperiodic treatments were given to the plants. Plants were grown in 80% shade, resulting in approximately 800 to 1200 foot candles of light. Measurements and numerical values represent averages of typical plant types.
Botanical classification: *Alocasia* hybrid 'ALO1'.

PROPAGATION

Root description: Thick, fleshy roots. True rhizomes not observed. Roots approximately 0.5 cm thick, colored near RHS White 155A.

PLANT

Growth habit: Rapid, upright. Basal leaves emerge in clumps.
Plant shape: Upright, petioles and leaves slightly arching out. No stems.
Height: Approximately 65 cm to top of foliar plane.
Plant spread: Approximately 65 cm in a 6 inch pot.
Pot size of plant described: 6 inch.
Growth rate: Rapid and vigorous.
Branching characteristics: No true branching. Leaves emerge direct from base of plant.
Number of clumps of leaves: 8.
Number of leaves per clump: Average 4 to 8.
Number of leaves per plant: Approximately 40 to 50.
Age of plant described: Approximately 6 months.

FOLIAGE

Leaf:
*Arrangement*.—Single leaves emerging basally.
*Largest, mature, fully expanded leaf*.—Length (excluding petiole): Range from 28 to 35 cm. Width: Range from 14 to 19.5 cm. Shape of blade: Sagittate, with two very deep lobes. Aspect: Slightly undulating, mainly flat. Apex: Apiculate. Base: Cordate, with 2 very deep lobes. Margin: Entire. Appearance: Glossy. Young foliage upper surface glossy. Texture of top surface: Smooth. Texture of bottom surface: Smooth. Color: Mature foliage upper side: Near RHS Green139A, but darker. Mature foliage under side: Near RHS Greyed-Purple N186C.

Venation:
*Type*.—Pinnate.
*Venation coloration upper side*.—Near RHS Green Greyed-Green 191D. Center most vein, just above petiole attachment RHS Green 137D.
*Venation coloration under side*.—Near RHS Green 138A. Outermost veins near margins near RHS Greyed-Purple N186C.

Petiole:
*Length*.—Approximate range between 45 and 57 cm.
*Width*.—At base: Approximately 1.6 cm. At leaf attachment: Approximately 0.6 cm.
*Color*.—Near RHS Greyed-Red 181D, heavily covered in short stripes near RHS Brown 200A and Yellow-Green 147A. Near leaf attachment, color changes to RHS Yellow-Green 145C, with stripes becoming less frequent, then absent approximately 1 cm from attachment point.
*Strength*.—Very strong.
*Texture*.—Glabrous.
*Other*.—Reduced sheath irregularly present.

Petiole sheath:
*Length*.—Approximately 5.5 cm.
*Width*.—Approximately 3.6 cm.
*Shape*.—Deltoid.
*Color*.—Near RHS Grey-Brown N199D.
*Texture*.—Glabrous, and papery.

Immature foliage:
*Length* (*excluding petiole*).—Range from 10 to 16 cm.
*Width*.—Range from 6 to 9 cm.
*Shape of blade*.—Cordate, with two very deep lobes, youngest leaves less deeply lobed.
*Aspect*.—Slightly undulating, mainly flat.
*Apex*.—Apiculate.
*Base*.—Cordate, with 2 very deep lobes.
*Margin*.—Entire.
*Appearance*.—Young foliage upper surface glossy, lower surface somewhat glossy.
*Texture of lop surface*.—Smooth.
*Texture of bottom surface*.—Smooth.
*Color*.—Young foliage upper side: Near RHS Green139A, apex near RHS Green 137A. Young foliage under side: Near RHS Green 137B.

Immature foliage venation:
*Type*.—Pinnate.
*Venation coloration upper side*.—Near RHS Green Greyed-Green 192B.
*Venation coloration under side*.—Near RHS Green 138A.

INFLORESCENCE

Not observed to date.

OTHER CHARACTERISTICS

Disease resistance: Greater resistance than typical of *Alocasia* to *Myrothecium* and leaf *Phytophthora* has been observed.
Drought tolerance and cold tolerance: The new cultivar is a typical *Alocasia*, cold tolerant to approximately 5° to 7° C. and does not tolerate drought.
Fruit/seed production: Not observed.

What is claimed is:

1. A new and distinct cultivar of *Alocasia* plant named 'ALO1' as herein illustrated and described.

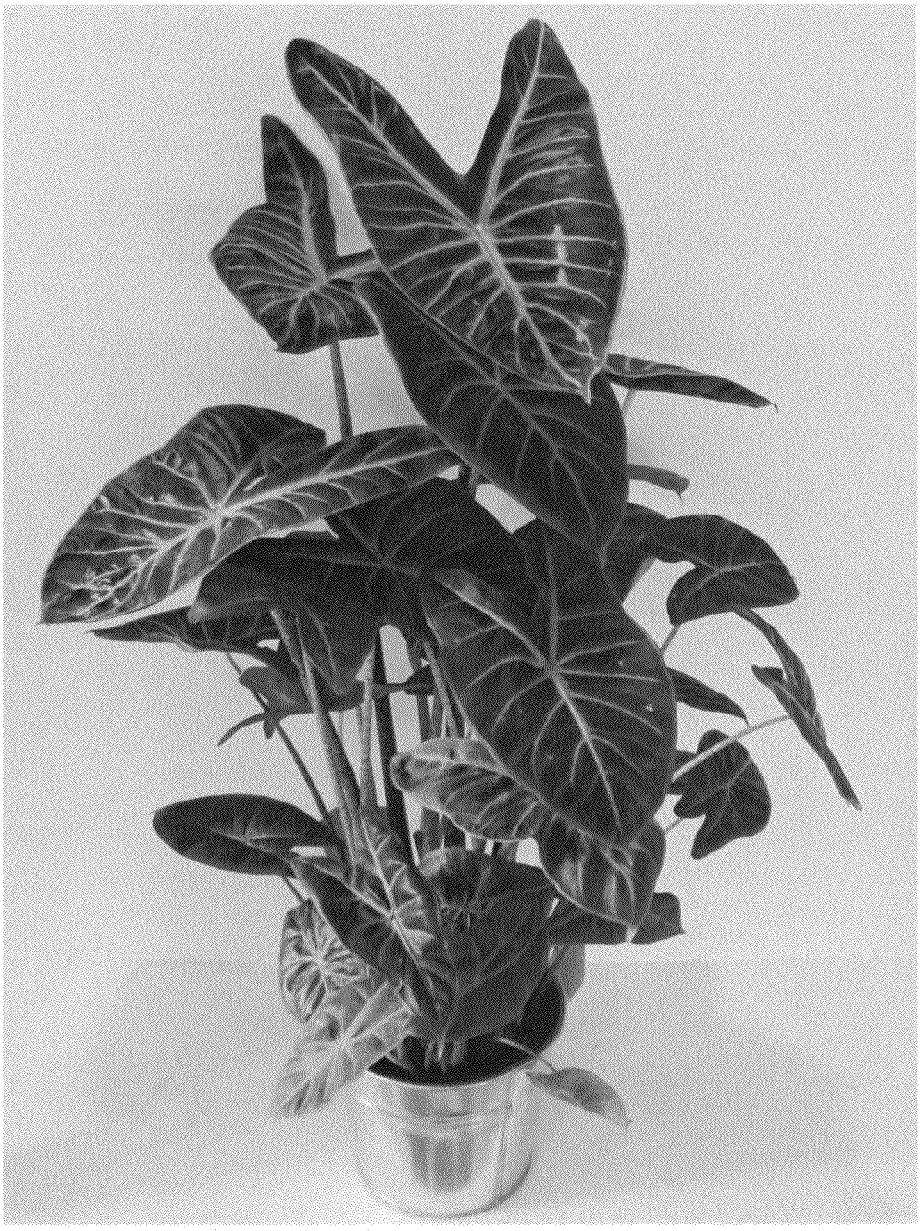

* * * * *